United States Patent
Dietl

(10) Patent No.: US 10,772,744 B2
(45) Date of Patent: Sep. 15, 2020

(54) ARTIFICIAL JOINT

(71) Applicant: OTTO BOCK HEALTHCARE PRODUCTS GMBH, Vienna (AT)

(72) Inventor: Hans Dietl, Gablitz (AT)

(73) Assignee: OTTO BOCK HEALTHCARE PRODUCTS GMBH, Vienna (AT)

( * ) Notice: Subject to any disclaimer, the term of this patent is extended or adjusted under 35 U.S.C. 154(b) by 273 days.

(21) Appl. No.: 15/753,670

(22) PCT Filed: Aug. 19, 2016

(86) PCT No.: PCT/EP2016/069724
§ 371 (c)(1),
(2) Date: Feb. 20, 2018

(87) PCT Pub. No.: WO2017/032717
PCT Pub. Date: Mar. 2, 2017

(65) Prior Publication Data
US 2018/0280163 A1    Oct. 4, 2018

(30) Foreign Application Priority Data

Aug. 24, 2015 (DE) .................. 10 2015 113 977

(51) Int. Cl.

| | |
|---|---|
| *A61F 2/68* | (2006.01) |
| *A61F 2/60* | (2006.01) |
| *A61F 2/64* | (2006.01) |
| *A61F 2/66* | (2006.01) |
| *A61F 5/01* | (2006.01) |
| *A61F 2/50* | (2006.01) |
| *A61F 2/74* | (2006.01) |

(52) U.S. Cl.
CPC ................ *A61F 2/68* (2013.01); *A61F 2/605* (2013.01); *A61F 2/64* (2013.01); *A61F 2/66* (2013.01); *A61F 2/6607* (2013.01); *A61F 5/0125* (2013.01); *A61F 5/0127* (2013.01); *A61F 2002/5072* (2013.01); *A61F 2002/6818* (2013.01); *A61F 2002/745* (2013.01); *A61F 2002/747* (2013.01); *A61F 2005/0155* (2013.01); *A61F 2005/0169* (2013.01); *A61F 2005/0179* (2013.01)

(58) Field of Classification Search
CPC .... A61F 2/68; A61F 2/605; A61F 2/64; A61F 2/66; A61F 2/6607; A61F 5/0125;
(Continued)

(56) References Cited

U.S. PATENT DOCUMENTS 5,549,712 A * 8/1996 Gammer ................. A61F 2/582
623/60
9,597,217 B2 * 3/2017 Patton ................... A61F 5/0102
(Continued)

FOREIGN PATENT DOCUMENTS

| | | |
|---|---|---|
| DE | 102008045113 A1 | 3/2010 |
| DE | 102012013140 A1 | 1/2014 |

(Continued)

OTHER PUBLICATIONS

PCT International Search Report for PCT International Patent Application No. PCT/EP2016/069724 dated Oct. 26, 2016.

*Primary Examiner* — Suba Ganesan
*Assistant Examiner* — Aren Patel
(74) *Attorney, Agent, or Firm* — Holland & Hart, LLP

(57) ABSTRACT

An artificial joint for lower extremities, comprising an upper part, which has mechanisms for attaching to a user, and a lower part mounted thereon in a pivotal manner about a joint axis. The lower part can be bent in from an extended position into a flexed position. A force accumulator is associated with the joint and is loaded via a force transmission mechanism through a flexing movement of the upper part relative to the lower part and supports an extension movement of the lower part relative to the upper part at least over a part of the extension movement. The force transmission device exerts a maximum moment of extension at a bending angle between 45° to 80°.

20 Claims, 3 Drawing Sheets

(58) Field of Classification Search
CPC ............ A61F 5/0127; A61F 2002/5072; A61F 2002/6818; A61F 2002/6854; A61F 2002/745; A61F 2002/747; A61F 2005/0169; A61F 2005/0179
USPC .......................................................... 623/26
See application file for complete search history.

(56) References Cited

U.S. PATENT DOCUMENTS

| | | |
|---|---|---|
| 2005/0059908 A1 | 3/2005 | Bogert |
| 2010/0312363 A1 | 12/2010 | Herr et al. |
| 2011/0071452 A1 | 3/2011 | Kuberger |
| 2011/0130846 A1* | 6/2011 | Kampas .................. A61F 2/64 623/39 |
| 2013/0245524 A1 | 9/2013 | Schofield |
| 2015/0150694 A1 | 6/2015 | Pusch et al. |
| 2016/0374834 A1 | 12/2016 | Mosier et al. |
| 2017/0027735 A1* | 2/2017 | Walsh .................. A61F 5/0102 |

FOREIGN PATENT DOCUMENTS

| | | |
|---|---|---|
| DE | 102013011080 A1 | 1/2015 |
| EP | 2316390 A1 | 5/2011 |
| EP | 1991180 B1 | 9/2012 |
| WO | 2009140956 A2 | 11/2009 |

* cited by examiner

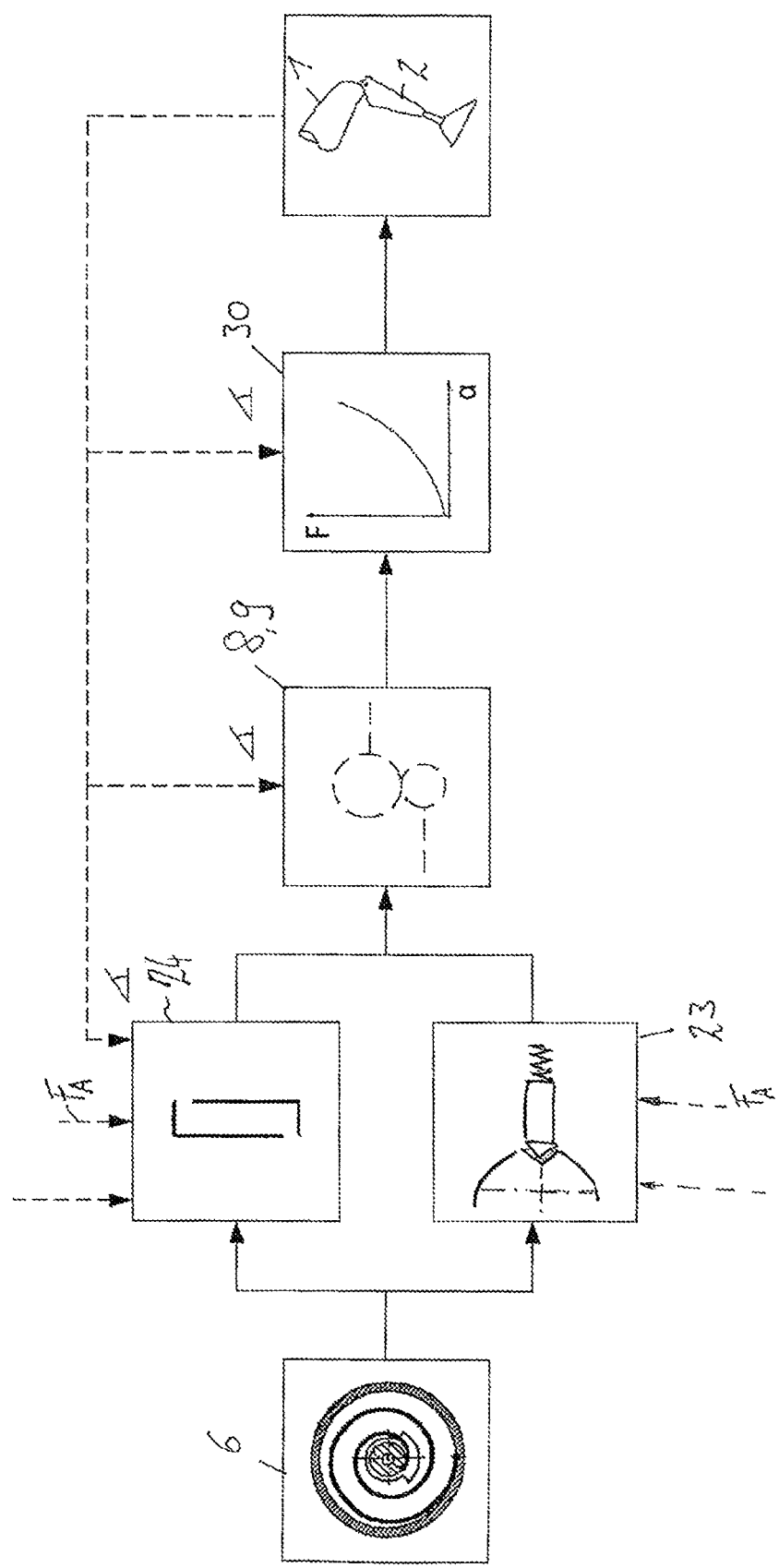

ARTIFICIAL JOINT

TECHNICAL FIELD

The invention relates to an artificial joint for lower extremities, with an upper part, which has mechanisms for securing to a user, and a lower part, which is mounted pivotably thereon about a joint axis and which can be flexed from an extended position to a flexed position during standing. The artificial joint can be designed as a hip joint and ankle joint. In a preferred embodiment, the artificial joint is designed as a knee joint.

BACKGROUND

Artificial joints for lower extremities can be used in orthoses or prostheses. Orthoses are needed to assist or maintain the function of the still present lower extremity. For this purpose, the orthoses are secured on the still present extremity. In the case of a knee orthosis, splints are placed on the upper leg and on the lower leg and are connected to each other via an orthotic knee joint. In the case of an ankle orthosis, the foot is fixed to a foot part, which is connected to a lower leg splint via an orthotic ankle joint. The same applies for a hip joint orthosis. In principle, it is also possible to provide an orthosis with more than two joints.

Missing limbs are replaced by prostheses. In the case of prosthetic knee joints, the missing knee joint is replaced by a prosthetic knee joint whose upper part is secured to an upper leg stump by an upper leg socket. The lower part is secured pivotably on the upper part of the prosthetic knee joint. A lower leg tube and a prosthetic foot, if appropriate with a prosthetic ankle joint, are arranged on the lower part. It is likewise possible, in cases of exarticulation of the hip, to replace the missing hip joint with a corresponding exo-prosthesis.

Patients with limited motoric abilities sometimes need assistance when performing movements that require force. These in particular include standing up or sitting down, since a considerable part of the body weight has to be moved vertically during these actions. When standing up, the body weight has to be lifted; when sitting down, it has to be lowered in a controlled manner. In the case of prosthesis users, the intact leg generally has to assume the entire work, optionally with the assistance of the arms. The situation is comparable in the case of orthosis users who have only limited motoric abilities in the treated leg.

SUMMARY

The object of the present invention is to make available an artificial joint which provides assistance in sitting down and standing up, without unwanted force being applied to the artificial joint in the seated position and restricting the user.

According to the invention, this object is achieved by an artificial joint having the features of the main claim. Advantageous embodiments and developments are disclosed in the subclaims, the description and the figures.

The artificial joint according to the invention for lower extremities, with an upper part, which has mechanisms for securing to a user, and a lower part, which is mounted pivotably thereon about a joint axis and which can be flexed from an extended position, in particular during standing, to a flexed position, is characterized in that the joint is assigned a force accumulator which is charged via a force transmission mechanism by a flexion movement of the upper part relative to the lower part and supports an extension movement of the lower part relative to the upper part at least over a part of the extension movement, wherein the force transmission mechanism exerts a maximum moment of extension at a flexion angle between 45° and 80°. In the extended state of the joint, the force accumulator is relaxed or only slightly pretensioned. During the flexion movement, a force transmission mechanism is activated via which the force accumulator is charged. When sitting down, for example, the loading assists the intact leg, since at least some of the energy that has to be expended when lowering the body is applied through the charging of the force accumulator. In a reverse movement, i.e. during the extension, the standing-up movement is assisted by the uncharging of the force accumulator. The force transmission mechanism is designed such that, in the range of the joint angle within which a maximum force would need to be exerted for the patient, namely at a flexion angle of between 45° and 80°, a maximum moment of extension is applied, such that, when standing up, maximum assistance is provided and, when sitting down, maximum damping or a counter force is applied. If the patient or user is seated, the joint is generally flexed at an angle of more than 80°, for example 90°, such that the maximum supporting moment is applied only in the angle range in which a movement actually takes place. At an angle of approximately 80°, the sitting down movement is concluded or the standing up movement has just begun. By designing the joint with a force accumulator, it is not necessary to provide motor drives. Instead, the energies applied can simply be converted and converted back again. The supporting moment is adjustable and is advantageously maintained at a level below the required moment for the intended movement, e.g. standing up or sitting down, in order to give the user control of the movement.

The joint is advantageously designed as an orthotic or prosthetic joint and can in particular be designed as a knee joint or hip joint.

An extension moment can be applied over the entire flexion range of the artificial joint, such that, at the very start of the flexion, a counteracting moment arises when a flexion takes place. This means that flexion of the relevant joint is possible only against an initial resistance. This has the effect that the patient acquires increased stability and safety in the extension position, for example when standing.

The force transmission mechanism is advantageously designed such that no extension moment applies at a flexion angle of over 90°, that is to say, after the extension moment maximum, the extension moment drops to zero or almost zero.

The force accumulator can be designed as a spring, spring assembly, hydraulic force accumulator or pneumatic force accumulator, which makes conversion to another energy form, for example electrical energy, unnecessary. The energy accumulated in the spring or in the spring assembly or in the pressure accumulators can be used directly for driving or exerting the extension moment, without the need for further components.

The force transmission mechanism can be assigned a blocking or releasing mechanism which, depending on the loading or position of the artificial joint, blocks the joint or interrupts a force transmission. Permanent support of the extension movement may be undesirable, for example if the lower part is unloaded or in the case of a seated position or a smooth surface. Therefore, blocking or releasing mechanisms are advantageous with which it is possible to block the joint or the force transmission or interrupt the force transmission according to the conditions of use of the artificial joint. The joint can be blocked by form-fit blocking of the movement of the upper part relative to the lower part, in which a blocking element engages in a recess.

The force transmission mechanism can also be active only over a defined flexion angle range, wherein the blocking or releasing mechanism interrupts the force transmission when a flexion angle is reached or blocks a movement of the artificial joint if force application is still present. A releasing mechanism of this kind can be designed as a release coupling, for example. The angle at which a release takes place can be adjustable. Similarly, the force level of the force accumulator can be adjustable in order to be able to permit adaptation to different patients with different weights or different physical capacities. By the release of the force transmission mechanism, the joint is freed and free mobility is permitted, such that, in the case of a knee joint for example, the small movements still performed when seated can be performed more or less without resistance. It is also possible that the joint is blocked, at least in the extension position, in order not to permit any extension at a defined position or loading situation.

In a development of the invention, provision is made that the blocking or releasing mechanism is assigned an actuator which deactivates the blocking or releasing mechanism when there is an axial force acting on the lower part or when an axial force acting on the lower part is exceeded. By virtue of the actuator working in a manner that is dependent on the load, it is ensured that extension support, for example of the hip joint or knee joint, is provided only when the person using the artificial joint applies a sufficiently high axial force to the lower part, in particular the foot, in order thereby to avoid slipping of the foot part or of the prosthetic foot. The actuator is advantageously a mechanical actuator and is itself actuated by the axial force. The actuator can be a slide, a push rod or also a piston of a hydraulic unit via which the axial force is conveyed to the blocking or releasing unit. The hydraulic unit allows force to be routed in almost any desired manner on account of the hydraulic lines and additionally permits a force transmission and/or travel transmission, resulting in greater freedom of design of the artificial joint.

In one embodiment, the artificial joint can be designed as an unlockable and lockable blocking knee joint, i.e. can have a locking mechanism that generally positively locks the joint against flexion. The locking mechanism can be unlocked manually or by motor in order to permit flexion.

In one embodiment of the invention, provision is made that several force accumulators are arranged in parallel or in series connection in order to optimally utilize the always small installation space, to permit modular production to permit individual adaptation to the respective patient and to permit removal or addition of force accumulators.

A gear can be arranged between the joint and the force accumulator.

The gear can be designed as a cam disk gear, lever gear, hydraulic gear or pneumatic gear.

In the position of the joint in which the maximum moment of extension applies, the force transmission direction of the force transmission mechanism can advantageously be perpendicular to the longitudinal extent of the upper part or of the lower part, in order to permit optimal utilization of the energy present in the force accumulator.

The force transmission mechanism can be designed as a push rod or as a flexible, non-elastic pulling means which is guided via rollers, journals or other deflection mechanisms in order to achieve an optimized force direction and re-direction adapted to the installation space.

In a development of the invention, provision is made for an elastic extension stop to be assigned to the artificial joint. The end point of the extension stop can be adjustable, such that the maximum extension position of the joint can be adapted individually to the user. Over a defined angle range before the maximum extension is reached, the extension movement is braked by an elastic component, as a result of which the moment acting in the direction of extension is reduced. This ensures, among other things, that the extension movement does not cease abruptly when the maximum extension is reached, as this would represent an unnatural movement.

BRIEF DESCRIPTION OF THE DRAWINGS

An illustrative embodiment of the invention is explained in more detail below with reference to the attached figures, where

FIG. 3 shows a schematic representation of a function chain.

DETAILED DESCRIPTION

Figure 1:
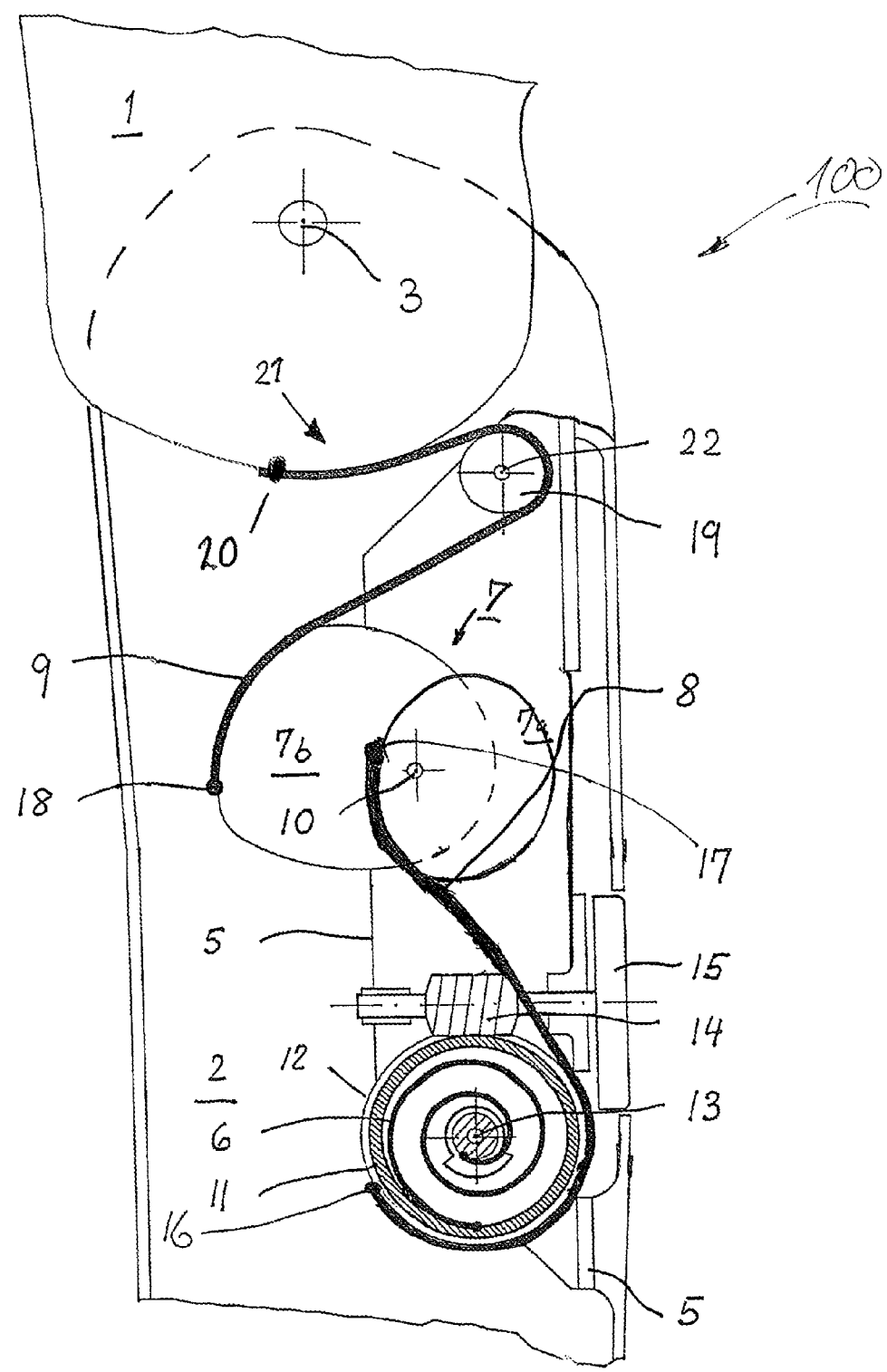
FIG. 1 shows a prosthetic knee joint in an extended position.

FIG. 1 shows an artificial joint 100 for lower extremities, with an upper part 1, which is mounted on a lower part 2 in such a way as to articulate about a pivot axis 3. Mechanisms for securing to a user or patient are arranged or formed on the upper part 1, the configuration of these mechanisms depending on the nature of the joint 100. If the artificial joint 100 is designed as an orthotic joint, the upper part 1 and the lower part 2 are designed as a splint arrangement which is fixed via straps, cuffs or other fastening means surrounding the limb that is to be supported. If the joint is designed as an ankle joint, the fixing is to the foot and to the lower leg. If the artificial joint is designed as an orthotic knee joint, the securing is at least to the lower leg and the upper leg. If the artificial joint is designed as a hip joint, the orthosis is secured to the trunk and to the upper leg. If the artificial joint 100 is designed as a prosthesis, the upper part 1 is fixed to the respective remaining limb via an adapter and a socket, for example via a lower leg socket to a lower leg, an upper leg socket to an upper leg in a design of the artificial joint as a prosthetic knee joint, or to the trunk if the artificial knee joint is designed as a hip joint. The respective lower part is then designed as a prosthetic foot, lower leg tube or upper leg tube.

In the embodiment according to FIG. 1, the artificial joint is designed as a prosthetic knee joint in which a force accumulator 6 in the form of a spiral spring is arranged in the lower part 2, the spiral spring being coupled to the upper part 1 via a force transmission in the form of belts or straps 8, 9 and a gear 7 in the form of a cam disk gear. The belt 9 assigned to the upper part 1 is flexible and non-elastic and, in the illustrated position of maximum extension of the prosthetic knee joint, is secured at a first securing point 20. The belt 9 bears on the substantially circular arc-shaped contour 21 of the distal end of the upper part 1, is deflected from there via a deflection roller 19 mounted rotatably about a rotation axis 22 in a separate module housing 5 inside the lower part 2, and bears with its second end on the cam disk gear 7 at a second securing point 18. The cam disk gear 7 is composed of two cam disks 7a, 7b which are mounted in the housing 5 in such a way as to be rotatable about a common pivot axis 10. The second belt 8 is mounted on the first cam disk 7a at a first securing point 17, the opposite end of the second belt 8 is secured at a second securing point 16 on a drive output disk 12, which is coupled to a spring housing 11 for the spiral spring 6. The drive output disk 12 is mounted in the housing 5 in such a way as to be pivotable about a rotation axis 13. All of the rotation and pivot axes 10, 13, 22 are oriented parallel to one another and extend substantially parallel to the pivot axis 3 of the artificial joint.

A worm wheel 14 is likewise mounted on the housing 5 and can be rotated via a manually actuated rotary disk 15. The worm wheel 14 meshes with a thread formed on the outer circumference of the spring housing 11, such that the pretensioning of the spiral spring 6 can be adjusted. By way of the pretensioning of the spiral spring 6, it is possible to adjust the tensile force, which is to be applied via the belts 8, 9, and therefore an extension moment, which also acts as a permanent extension moment and is directed against a flexion of the artificial joint 100. When the adjusted pretensioning of the spiral spring 6 is great enough, a basic resistance to flexion is obtained and the person using the artificial joint therefore feels safer. Both belts 8, 9 are fixed on the outer circumference of the respective cam disk 7a, 7b. The cam disks have an eccentric contour about the rotation axis 10, wherein the contours of both cam disks 7a, 7b are different from each other such that, with an almost constant restoring force, the tensioning inside the spiral spring 6 ensures an extension moment that changes over the flexion angle of the upper part 1 relative to the lower part 2. The extension moment depends on the respective lever ratios and distances of the belts 8, 9 from the pivot axis 10 and the first securing point 20 of the belt 9 on the upper part 1 and the position of the deflection roller 19. The gear 7 is designed in conjunction with the spiral spring 6 in such a way that, depending on the flexion angle of the upper part relative to the lower part 2, the profile of the torque applied about the pivot axis 3 has a maximum value in a flexion range between 45° and 80° and, upon further flexion beyond this target angle range, decreases sharply. A torque that counteracts the flexion is limited, in a first angle range between a full knee extension and a flexion of up to approximately 20°, to 20% of the maximum possible torque assistance. Once a flexion angle of ca. 25° is reached, the resistance moment rises sharply and reaches its maximum at joint angles in the range of ca. 80°, wherein an almost constant moment level applies in the range between 45° and 80°. After the joint angle of 0° is reached, the extension moment decreases steeply, in which case preferably the force accumulator 6 in the form of the spiral spring is separated from the force transmission mechanism 8, 9, or the cam disk gear 7 is designed such that only a minimal extension moment is applied as from an angle setting of 90°.

Figure 2:
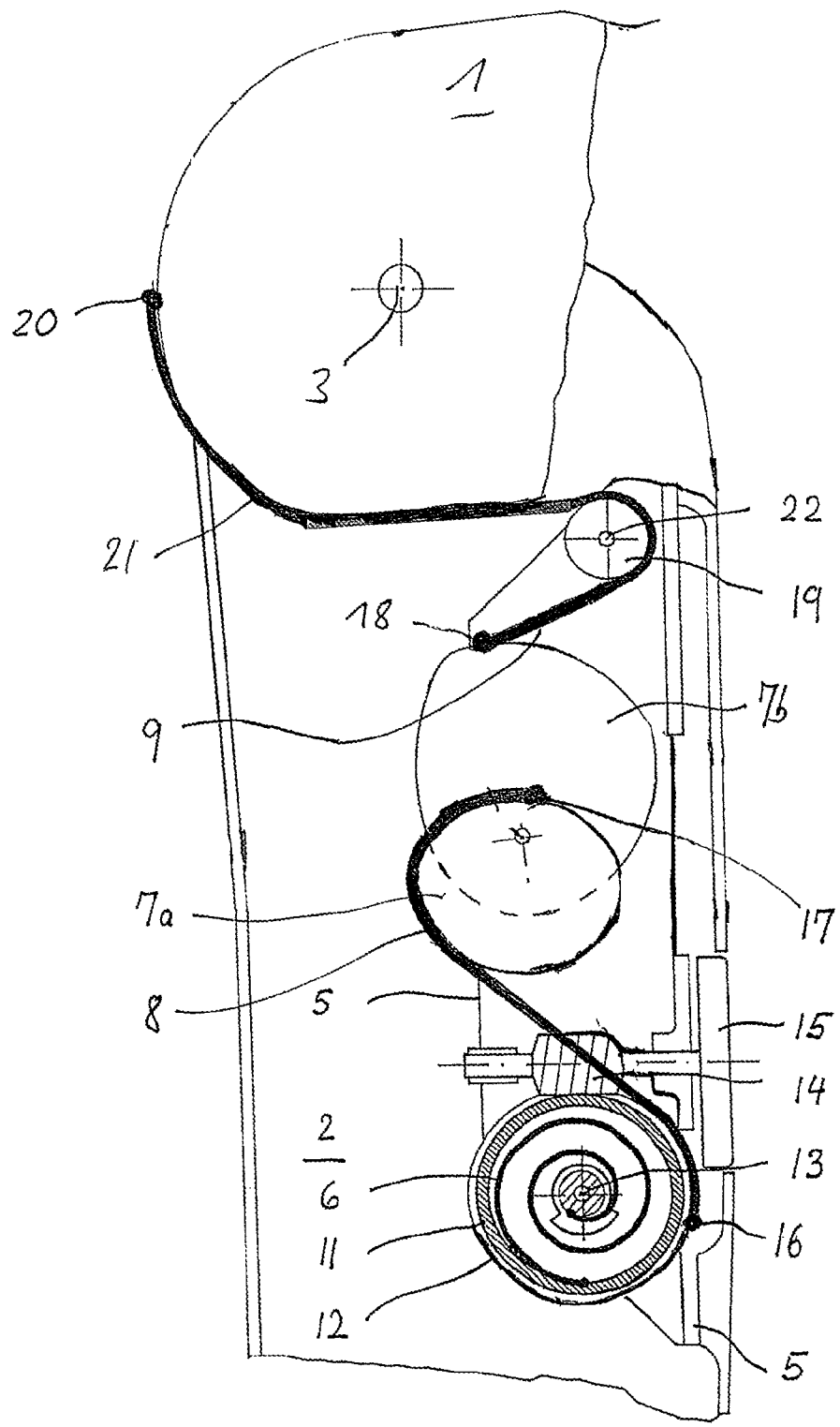
FIG. 2 shows a joint according to FIG. 1 in a flexed position.

FIG. 2 shows the artificial joint in a flexed position in which the upper part 1 is pivoted about the pivot axis 3 to almost a right angle to the lower part 2. The cam disk gear 7 has been pivoted clockwise, and the spiral spring 6 has been wound up and charged counterclockwise via the drive disk 2. In the 90° position shown, a force transmission between the force accumulator, in the form of the spiral spring 6, and the force transmission mechanism 8, 9 can be interrupted via a release coupling, such that in this position, and upon further flexion, no extension moment is applied, i.e. a force effecting the extension of the upper part 1 relative to the lower part 2. If an extension is then initiated, a force transmission then once again intervenes starting from a predetermined angle, for example at a joint angle of 80°, and the force accumulator 6 assists the extension movement with a maximum moment of extension in an angle range between 45° and 80°. Upon further extension, i.e. reduction of the joint angle, the extension moment decreases, on account of the geometries of the cam disks 7a, 7b of the cam gear 7, as far as a predetermined value which can be variably adjusted. The adjustment is effected via the rotary wheel 15 and the pretensioning via the worm gear 14 and the pretensioning of the spiral spring 6.

The joint mechanism can also be designed as a blocking joint with a separate form-fit blocking mechanism, such that an extension movement, i.e. a flexion, can take place only after release of the blocking mechanism.

FIG. 3 shows a schematic representation of a function chain of individual components of the artificial joint. An energy or force accumulator 6, for example in the form of a spiral spring, a pneumatic or hydraulic pressure accumulator, another spring accumulator or the like, is connected to at least one force transmission mechanism 8, 9 via a blocking mechanism 23 or via a release mechanism 24. The force transmission mechanism 8, 9 is connected to a progressive, elastic joint stop 30, which is designed in particular as an extension stop, in order to prevent abrupt striking of the lower part 2 against the upper part 1 in the extension position. The extension resistance is increased, advantageously progressively increased, over a defined angle range prior to complete extension, such that uncontrolled extension is avoided.

The force accumulator 6 can be designed according to the embodiment in FIGS. 1 and 2. The blocking mechanism 23, likewise the release mechanism 24 or coupling, can be switched according to an axial force FA which acts in or on the lower part 2. In order to prevent a situation where, on account of an insufficient axial force acting on the lower part 2 or on the prosthetic foot, the lower part 2 is advanced to the extension position by the force accumulator 6, the energy transmission from the force accumulator 6 to the upper part 1 or lower part 2 via the force transmission mechanism 8, 9 is permitted only when the foot part forms a sufficient abutment, i.e. the person using the artificial joint is standing or sits with sufficient loading. When sitting without loading, no axial force or virtually no axial force acts in the lower part 2, such that force transmission from the energy accumulator for the extension of the joint is blocked. As an alternative to a blocking by the blocking mechanism 23, this can also be effected by the release mechanism 24 or a switchable coupling. When a sufficiently high axial force is detected inside the lower part 2, it can be assumed that the patient would like to stand up or is standing, such that assistance in standing up or extension assistance is expedient.

Alternatively or in addition to consideration of the axial force FA, a blocking mechanism 23 or a release device 24 or coupling can be activated or deactivated individually by a signal from the user, as is indicated by the arrows. The activation can be done mechanically, or electronically by operation of a switch. The blocking mechanism 23 and the release mechanism 24 are thus designed as switchable components which can be switched either automatically, when a limit value of the axial force for example is reached, or individually by the user.

Both the release device 24 and the blocking device 23 are switchable or controllable according to the joint angle. Thus, the force can be transmitted via the release device over a defined angle range completely via the release device or the blocking device 23 can be activated or deactivated over a defined angle range. For example, in the end region of the extension, there can be a reduced force transmission from the energy accumulator 6 to the artificial joint in order to avoid too hard a stop at the maximum extension. Likewise, the force transmission mechanism 8, 9 can be made effective depending on the angle, and this can be ensured by a special arrangement and, if appropriate, adjustability of the respective components of the force transmission mechanism. The stop 30 can be adjusted via the joint angle. The greater the joint angle, i.e. the angle enclosed between the longitudinal extent of the upper part and the longitudinal extent of the lower part, the greater the resistance in the elastic stop can be.

The invention claimed is:

1. An artificial joint for lower extremities, comprising:
   an upper part, which has mechanisms for securing to a user;
   a lower part, which is mounted pivotably to the upper part about a joint axis and which can be flexed from an extended position to a flexed position;
   a force accumulator, which is charged via a force transmission mechanism by a flexion movement of the upper part relative to the lower part and supports an extension movement of the lower part relative to the upper part at least over a part of the extension movement;
   wherein the force transmission mechanism exerts a maximum moment of extension at a flexion angle between 45° and 80°.

2. The artificial joint as claimed in claim 1, wherein the joint is designed as an orthotic joint or prosthetic joint.

3. The artificial joint as claimed in claim 1, wherein the joint is designed as a knee joint or hip joint.

4. The artificial joint as claimed in claim 1, wherein an extension moment applies over an entire flexion range.

5. The artificial joint as claimed in claim 1, wherein no extension moment applies at a flexion angle of over 90°.

6. The artificial joint as claimed in claim 1, wherein the force accumulator is designed as a spring, spring assembly, hydraulic force accumulator or pneumatic force accumulator.

7. The artificial joint as claimed in claim 1, wherein the force transmission mechanism is assigned a blocking or releasing mechanism which, depending on a loading or position of the artificial joint, blocks an extension or interrupts force transmission.

8. The artificial joint as claimed in claim 7, wherein the force transmission mechanism is active only over a defined flexion angle range, and the blocking or releasing mechanism blocks the artificial joint or interrupts the force transmission when a defined flexion angle is reached.

9. The artificial joint as claimed in claim 7, wherein the blocking or releasing mechanism is assigned an actuator which deactivates the blocking or releasing mechanism when an axial force acting on the lower part is present or is exceeded.

10. The artificial joint as claimed in claim 7, wherein the releasing mechanism is designed as a switchable coupling.

11. The artificial joint as claimed in claim 1, wherein a force level of the force accumulator is adjustable.

12. The artificial joint as claimed in claim 1, wherein the joint is designed as an unlockable and lockable blocking joint.

13. The artificial joint as claimed in claim 1, wherein several force accumulators are arranged in parallel or in series connection.

14. The artificial joint as claimed in claim 1, further comprising a gear.

15. The artificial joint as claimed in claim 14, wherein the gear is designed as a cam disk gear, lever gear, hydraulic gear or pneumatic gear.

16. The artificial joint as claimed in claim 1, wherein in a position of the joint in which the maximum moment of extension applies, a force application direction of the force transmission mechanism is perpendicular to a longitudinal extent of the upper part or of the lower part.

17. The artificial joint as claimed in claim 1, wherein the force transmission mechanism is designed as a push rod or a flexible pulling means.

18. The artificial joint as claimed in claim 1, further comprising an elastic extension stop which, in a defined angle range, brakes the extension movement before the maximum extension is reached.

19. An artificial joint for lower extremities, the artificial joint comprising:
   an upper part having at least one fastener configured to secure the upper part to a user;
   a lower part mounted pivotably to the upper part about a joint axis, the lower part being movable between an extended position and a flexed position;
   a force transmission mechanism supporting an extension movement of the lower part relative to the upper part at least over a part of an extension movement, the force transmission mechanism exerts a maximum moment of extension at a flexion angle between 45° and 80°;
   a force accumulator, which is charged via the force transmission mechanism by a flexion movement of the upper part relative to the lower part.

20. The artificial joint as claimed in claim 19, wherein the joint is designed as an orthotic joint or prosthetic joint.

* * * * *